(12) United States Patent
Remmereit et al.

(10) Patent No.: US 9,708,208 B2
(45) Date of Patent: *Jul. 18, 2017

(54) ENERGY PRODUCTION WITH HYPERTHERMOPHILIC ORGANISMS

(75) Inventors: Jan Remmereit, Hovdebygda (NO); Michael Thomm, Regensburg (DE)

(73) Assignee: HYPERTHERMICS HOLDING AS, Hovdebygda (NO)

( * ) Notice: Subject to any disclaimer, the term of this patent is extended or adjusted under 35 U.S.C. 154(b) by 983 days.

This patent is subject to a terminal disclaimer.

(21) Appl. No.: 11/879,710

(22) Filed: Jul. 18, 2007

(65) Prior Publication Data

US 2008/0131958 A1   Jun. 5, 2008

Related U.S. Application Data

(60) Provisional application No. 60/831,635, filed on Jul. 18, 2006.

(51) Int. Cl.

| | |
|---|---|
| *C12P 5/02* | (2006.01) |
| *C02F 3/34* | (2006.01) |
| *B09B 3/00* | (2006.01) |
| *C12M 1/02* | (2006.01) |
| *C12P 3/00* | (2006.01) |
| *C12P 7/06* | (2006.01) |
| *C12M 1/00* | (2006.01) |
| *B09C 1/10* | (2006.01) |

(52) U.S. Cl.
CPC ............... *C02F 3/34* (2013.01); *B09B 3/00* (2013.01); *B09C 1/10* (2013.01); *C12M 41/18* (2013.01); *C12M 43/08* (2013.01); *C12P 3/00* (2013.01); *C12P 5/023* (2013.01); *C12P 7/065* (2013.01); *C02F 2301/106* (2013.01); *Y02E 50/16* (2013.01); *Y02E 50/17* (2013.01); *Y02E 50/343* (2013.01); *Y02P 20/129* (2015.11); *Y02P 20/136* (2015.11); *Y02W 10/33* (2015.05); *Y02W 10/37* (2015.05)

(58) Field of Classification Search
CPC .. C02F 3/34; C02F 2301/10; C02F 2301/106; C12P 3/00; C12P 5/023
USPC ............... 435/168, 170, 262, 292.1, 300.1; 210/603; 47/1.4
IPC ............................................. C12P 3/00,5/023
See application file for complete search history.

(56) References Cited

U.S. PATENT DOCUMENTS

| | | | |
|---|---|---|---|
| 3,676,363 A | 7/1972 | Mosier | |
| 4,530,956 A | 7/1985 | Ugelstad | |
| 4,540,666 A | 9/1985 | Nukina et al. | |
| 4,787,455 A | 11/1988 | Snavely, Jr. | |
| 4,986,353 A | 1/1991 | Clark | |
| 4,986,354 A | 1/1991 | Cantu | |
| 5,000,000 A | 3/1991 | Ingram et al. | |
| 5,354,878 A | 10/1994 | Connemann | |
| 5,486,068 A | 1/1996 | Wilson | |
| 5,525,229 A | 6/1996 | Shih | |
| 5,624,841 A | 4/1997 | Raven et al. | |
| 5,661,017 A | 8/1997 | Dunahay | |
| 5,910,254 A | 6/1999 | Guelcher | |
| 6,000,551 A | 12/1999 | Kanel | |
| 6,299,774 B1 * | 10/2001 | Ainsworth et al. | 210/603 |
| 6,524,486 B2 | 2/2003 | Borodyanski | |
| 6,555,350 B2 | 4/2003 | Ahring et al. | |
| 7,001,519 B2 | 2/2006 | Linden | |
| 2003/0211594 A1 | 11/2003 | Rosebrook | |
| 2004/0035785 A1 | 2/2004 | Rebholz | |
| 2004/0121447 A1 | 6/2004 | Fournier | |
| 2005/0026262 A1 | 2/2005 | Yoshitani et al. | |
| 2005/0061737 A1 | 3/2005 | Linden et al. | |
| 2005/0064577 A1 * | 3/2005 | Berzin | 435/266 |
| 2005/0115893 A1 | 6/2005 | Brune et al. | |
| 2008/0311640 A1 * | 12/2008 | Cox et al. | 435/168 |

FOREIGN PATENT DOCUMENTS

| | | | |
|---|---|---|---|
| EP | 0193369 | | 9/1986 |
| EP | 0656459 | | 6/1995 |
| JP | 08308587 A | * | 11/1996 |
| JP | 2003 116589 | | 4/2003 |
| JP | 2003326237 A | * | 11/2003 |
| WO | 96/27070 | | 9/1996 |
| WO | 97/45625 | | 12/1997 |
| WO | 99/19375 | | 4/1999 |
| WO | 99/36667 | | 7/1999 |
| WO | 99/54592 | | 10/1999 |
| WO | 00/53791 | | 9/2000 |
| WO | 02/06503 | | 1/2002 |
| WO | WO 2006056819 A1 | * | 6/2006 |
| WO | 2008/053353 | | 5/2008 |

OTHER PUBLICATIONS

English Language machine translation of JP 08-308587 (Nov. 26, 1996).*
English Language machine translation of JP 2003-326237 (Nov. 18, 2003).*
Van Groenestijn, J.W., et al; "Energy aspects of biological hydrogen production in high rate bioreactors operated in the thermophilic temperature range"; International Journal of Hydrogen Energy, Elsevier Science (Nov. 1, 2002); Vo. 27, No. 11-12, pp. 1141-1147.
Eichler, Jerry; "Biotechnological uses of archaeal extremozymes"; Biotechnology Advances, Elsevier Science, (Jul. 1, 2001); vol. 19, No. 4, pp. 261-278.
Kanai, Tamotsu, et al.; "Continuous hydrogen production by the hyperthermophilic archaeon, Thermococcus Kodakaraensis KOD1"; Journal of Biotechnology, Elsevier Science, (Mar. 30, 2005); vol. 116, No. 3, pp. 271-282.

(Continued)

*Primary Examiner* — William H Beisner
(74) *Attorney, Agent, or Firm* — Casimir Jones S.C.

(57) ABSTRACT

The present invention relates to the field of degradation with hyperthermophilic organisms, and in particular to the use of hyperthermophilic degradation to produce heat from a biomass. In some embodiments, a biomass is fermented in the presence of hyperthermophilic organisms to produce heat. The heat is used to heat a liquid which is used directly in a heat pump or radiant heat or to produce electricity or drive a steam turbine.

7 Claims, No Drawings

(56) References Cited

OTHER PUBLICATIONS

Bringer-Meyer et al., (1986), "Pyruvate decarboxylase from Zymomonas mobilis. Isolation and partial characterization" Arch. Microbiol. 146:105-110.
Brau et al., (1986), "Cloning and expression of the structural gene for pyruvate decarboxylase of Zymomonas mobilis in *Escherichia coli*." Arch. Microbiol. 144:296-301.
Chinese Office Action dated Aug. 30, 2010 from CN Patent Application No. 200780030825.6.
Chou, et al., "Hydrogenesis in hyperthermophilic microorganisms: Implications for Biofuels," Metabolic Engineering, vol. 10, Jun. 28, 2008, pp. 394-404.
Conway et al., (1987), "Cloning and sequencing of the alcohol dehydrogenase II gene from Zymomonas mobilis." J. Bacteriol. 169:2591-2597.
Conway et al., (1987), "Promoter and nucleotide sequences of the Zymomonas mobilis pyruvate decarboxylase." J. Bacteriol. 169:949-954.
Eichler, Jerry; "Biotechnological uses of archaeal extremozymes"; Biotechnology Advances (2001); vol. 19, pp. 261-278.
Eriksen, et al., "Hydrogen production in anaerobic and microaerobic thermotoga neapolitana," Biotechnology Letters, vol. 30, Sep. 12, 2007, pp. 103-109.
Examiner's First Report on AU Patent Application No. 2007315860 dated Feb. 23, 2010.
Ingram et al., (1987), "Genetic engineering of ethanol production in *Escherichia coli*." Appl. Environ. Microbiol. 53:2420-2425.
Ingram et al., (1988), "Expression of Different Levels of Ethanologenic Enzymes from Zymomonas mobilis in Recombinant Strains of *Escherichia coli*." Appl. Environ. Microbiol. 54:397-404.
International Search Report dated Jan. 15, 2009, International Patent Application No. PCT/IB2007/003772.
Kanai, T., et al., "Continuous Hydrogen Production by the Hyperthermophilic Archaeon, Thermococcus Kodakaraensis KOD1", Journal of Biotechnology, Elsevier Science Publishers, Amsterdam, NL, vol. 116, No. 3, Mar. 30, 2005, pp. 271-282.
Kengen, et al., "Growth and energy conservation in batch cultures of pyrococus furiosus," FEMS Microbiology Letters, vol. 117, 1994, pp. 305-310.
Neale et al., (1987), "Nucleotide sequence of the pyruvate decarboxylase gene from Zymomonas mobilis." Nucleic Acid. Res. 15:1753-1761.
van Groenestijn, J.W., et al.; "Energy aspects of biological hydrogen production in high rate bioreactors operated in the thermophilic temperature range"; International Journal of Hydrogen Energy (2002); vol. 27, pp. 1141-1147.

Woodward, et al., "Efficient hydrogen production using enzyes of the pentose phosphate pathway," Proceedings of the 2002 U.S. DOE hydrogen program review (2002), pp. 1-12.
Smith, W., et al., "Methane from biomass and waste—a program review". TERI Information Digest on Energy 2(1): 1-20 (1992).
EP Search Report mailed Oct. 15, 2013 from EP Patent Application No. 13168386.4.
CN Office Action mailed Nov. 22, 2012 for CN Patent Application No. 200780030825.6.
Hao, Ruixia, et al., "Effect on crude oil by thermophilic bacterium," Journal of Petroleum Science and Engineering 43 (2004) 247-258.
Ahring, Birgitte, et al., "Methanogenesis from acetate: physiology of a thermophilic, acetate-utilizing methanogenic bacterium," FEMS Microbiology Letters 28 (1985) 15-19.
Blumer-Schuette, Sara E., et al., "Extremely thermophilic microorganism for biomass conversion: status and prospects," Current Opinion in Biotechnology (2008), 19: 210-217.
Santangelo, Thomas J., et al., "Shuttle Vector Expression in Thermococcus kodakaraensis: Contributions of cis Elements to Protein Synthesis in a Hyperthermophilic Archaeon," Applied and Environmental Microbiology, May 2008, pp. 3099-3104.
Waege, Ingrid, "Shuttle vector-based transformation system for Pyrococcus furiosus," Applied and Environmental Microbiology, May 2010, vol. 76, No. 10, pp. 3808-3313.
Lucas, Soizick, et al., "Construction of a shuttle vector for, and spheroplast transformation of, the hyperthermophilic Archaeon Pyrococcus abyssi," Applied and Environmental Microbiology, Nov. 2002, vol. 68, No. 11, pp. 5528-5536.
Hethke, Carina, et al., "A cell-free transcription system for the hyperthermophilic archaeon Pyrococcus furiosus," Nucleic Acids Research, Jun. 15, 1996, vol. 24, No. 12, Jun. 15, 1996, pp. 2369-2376.
Large, Andrew, "Characterization of a tightly controlled promoter of the halophilic archaeon Haloferax volcanii and its use in the analysis of the essential cct1 gene," Molecular Microbiology, Dec. 2007, vol. 66, No. 5, pp. 1092-1106.
Vazhappilly, et al., "Heterotrophic Production Potential of Omega-3 Polyunsaturated Fatty Acids by Microalgae and Algae-like Microorganisms," Botanica Marina, vol. 41 (1998), pp. 553-558.
Schroder et al., "Glucose fermentation to acetate, CO2, and H2 in the anaerobic hyperthermophilic eubacterium Termatoga maritime: involvement of the Embden-Meyerhof pathway," Arch Microbiol (1994) 161: 460-470.
CN Office Action mailed Aug. 14, 2014, CN Patent Application No. 201310433718.5.
Bergquist et al. "Molecular diversity of thermophilic and hemicellulolytic bacteria", FEMS Microbiology Ecology, vol. 28, No. 2, Feb. 1999, pp. 99-110.
Mussatto et al. "Brewers' spent grain: generation, characteristics and potential applications", Journal of Cereal Science, Academic Press LTD, vol. 43, No. 1, 2006, pp. 1-14.

* cited by examiner

ENERGY PRODUCTION WITH HYPERTHERMOPHILIC ORGANISMS

This application claims the benefit of U.S. Prov. Appl. 60/831,635 filed Jul. 18, 2006 incorporated by reference herein in its entirety.

FIELD OF THE INVENTION

The present invention relates to the field of degradation with hyperthermophilic organisms, and in particular to the use of hyperthermophilic degradation to produce heat from a biomass.

BACKGROUND OF THE INVENTION

The cost of conventional energy sources has increased dramatically in the last few years, and the use of many conventional energy sources such as oil, coal and nuclear power has been demonstrated to be harmful to the environment.

Many clean alternative energy sources have been developed or proposed. Such sources include solar energy, geothermal energy, wind energy, hydroelectric energy, hydrogen reactors and fuel cells. However, many of these sources are either expensive (solar energy) or limited by geographical concerns (geothermal, wind and hydropower).

Other alternative energy sources make use of biomass. However, those systems often involve the production of a secondary product such as ethanol or involve combusting the materials. These methods suffer from problems including contamination of the environment and requiring the use of valuable farmland to produce biomass.

Accordingly, what is needed in the art is alternative systems to utilize waste biomass materials or naturally available biomass materials to produce heat or electricity.

SUMMARY OF THE INVENTION

The present invention relates to the field of degradation with hyperthermophilic organisms, and in particular to the use of hyperthermophilic degradation to produce heat from a biomass. In some embodiments, the present invention provides a system comprising: a bioreactor, the bioreactor containing biomass and a population of at least one genus of hyperthermophilic organisms; and an energy transfer system. In some embodiments, the hyperthermophilic organisms are anaerobic hyperthermophilic organisms. In some preferred embodiments, the anaerobic hyperthermophilic organisms are selected from the group consisting of the genera *Pyrococcus, Thermococcus, Palaeococcus, Acidianus, Pyrobaculum, Pyrodictium, Pyrolobus, Methanopyrus, Methanothermus,* hyperthermophilic Methanococci like *Mc. jannaschii, Fervidobacterium* and *Thermotoga,* and combination thereof. In other embodiments, the hyperthermophilic organisms are aerobic hyperthermophilic organisms selected from the genera *Thermus, Bacillus,* and *Thermoactinomyces*. In still other embodiments, the aerobic hyperthermophilic organisms are selected from the group consisting of *Aeropyrum pernix, Metallosphaera sedula* and other *Metallosphaera* species *Sulfolobus solfataricus, Sulfobus tokodaii, Thermoplasma acidophilum* and *Thermoplasma volcanium,* and combinations thereof. In some embodiments, the biomass is supplemented with a cell culture media component selected from the group consisting of a mineral source, vitamins, amino acids, an energy source, and a microorganism extract.

In some embodiments, the energy transfer system is selected from the group consisting of a fuel cell, a combustion unit, a thermocouple, and a heat transfer system. In further embodiments, the combustion unit comprises a steam powered system. In still further embodiments, the steam powered system is a steam turbine or generator. In some embodiments, the heat transfer system comprises a heat pump. In some embodiments, the energy transfer system is a thermocouple and wherein the energy transfer system further comprises an electrolysis system that coverts water into hydrogen and oxygen. In some preferred embodiments, the biomass is selected from the group consisting of sewage, agricultural waste products like corn steep liquor and soybean hulls, brewery grain by-products, food waste, organic industry waste, forestry waste, crops, grass, seaweed, plankton, algae, fish, fish waste, and combinations thereof.

In some embodiments, the present invention provides methods comprising: a) providing a biomass and a population of at least one genus of a hyperthermophilic organism; b) fermenting the biomass in the presence of the population of at least one genus of a hyperthermophilic organism under conditions such that heat is produced; c) using the heat to produce electricity or heat a liquid. In some embodiments, the hyperthermophilic organisms are anaerobic hyperthermophilic organisms. In some preferred embodiments, the anaerobic hyperthermophilic organisms are selected from the group consisting of the genera *Pyrococcus, Thermococcus, Palaeococcus, Acidianus* (*Aeropyrum* and *Sulfolobus* are not anaerobic!) *Pyrobaculum, Pyrodictium Pyrolobus, Methanopyrus, Methanothermus,* hyperthermophilic Methanococci like *Mc. jannaschii Fervidobacterium,* and *Thermotoga,* and combination thereof. In other embodiments, the hyperthermophilic organisms are aerobic hyperthermophilic organisms selected from the genera *Thermus, Bacillus,* and *Thermoactinomyces*. In still other embodiments, the aerobic hyperthermophilic organisms are selected from the group consisting of *Aeropyrum pernix, Sulfolobus solfataricus, Metallosphaera sedula, Sulfobus tokodaii, Thermoplasma acidophilum* and *Thermoplasma volcanium,* and combinations thereof. In some preferred embodiments, the biomass is selected from the group consisting of sewage, agricultural waste products like corn steep liquor and soybean hulls, brewery grain by-products, food waste, organic industry waste, forestry waste, crops, grass, seaweed, plankton, algae, fish, fish waste, and combinations thereof. In some embodiments, the biomass is supplemented with a cell culture media component selected from the group consisting of a mineral source, vitamins, amino acids, an energy source, and a microorganism extract.

In some embodiments, the liquid is water and the heating produces steam. In some embodiments, the steam is used to drive a steam turbine to produce electricity. In further embodiments, the heated liquid is transferred to a building for radiant heat. In some embodiments, the electricity is produced via a thermocouple. In further embodiments, the electricity is used for electrolysis of water. In some embodiments, the liquid is transferred to a heat pump.

In some embodiments, the present invention further provides methods comprising: a) providing a biomass and a population of at least one genus of a hyperthermophilic organism; and b) degrading the biomass in the presence of the population of at least one genus of a hyperthermophilic organism under conditions such that degradation products are produced. In some preferred embodiments, the anaerobic hyperthermophilic organisms are selected from the group consisting of the genera *Pyrococcus, Thermococcus,*

*Palaeococcus, Acidianus, Pyrobaculum, Pyrolobus, Pyrodictium, Methanopyrus, Methanothermus,* hyperthermophilic *Methanococci* like *Mc. jannaschii Fervidobacterium* and *Thermotoga*, and combination thereof. In other embodiments, the hyperthermophilic organisms are aerobic hyperthermophilic organisms selected from the genera *Thermus, Bacillus*, and *Thermoactinomyces*. In still other embodiments, the aerobic hyperthermophilic organisms are selected from the group consisting of *Aeropyrum pernix, Sulfolobus solfataricus, Sulfobus tokodaii, Metallosphaera sedula, Thermoplasma acidophilum* and *Thermoplasma volcanium*, and combinations thereof. In some preferred embodiments, the biomass is selected from the group consisting of sewage, agricultural waste products, brewery grain by-products, food waste, organic industry waste, forestry waste, crops, grass, seaweed, plankton, algae, fish, fish waste, and combinations thereof. In some embodiments, the biomass is supplemented with a cell culture media component selected from the group consisting of a mineral source, vitamins, amino acids, an energy source, and a microorganism extract. In some further preferred embodiments, the degradation products are selected from the group consisting of hydrogen, methane and ethanol. In some embodiments, the methods further comprise the step of converting the degradation products into energy. In some embodiments, the methods further comprise the step of using the hydrogen in a fuel cell. In some embodiments, the methods further comprise the step of using the methane or ethanol in a combustion unit.

In some embodiments, the present invention provides methods for reducing carbon dioxide emissions comprising: a) providing a biomass and a population of at least one genus of a hyperthermophilic organism; b) anaerobically degrading said biomass in the presence of said population of at least one genus of a hyperthermophilic organism to produce substrates for energy production; and c) producing energy from said substrates, wherein carbon dioxide emissions are reduced as compared to aerobic degradation of said biomass materials. In further embodiments, the present invention provides methods for generating carbon credits comprising: a) providing a biomass and a population of at least one genus of a hyperthermophilic organism; b) anaerobically degrading said biomass in the presence of said population of at least one genus of a hyperthermophilic organism to produce substrates for energy production, and c) producing energy from said substrates under conditions such that carbon credits are generated.

DEFINITIONS

As used herein, the term "biomass" refers to biological material which can be used as fuel or for industrial production. Most commonly, biomass refers to plant matter grown for use as biofuel, but it also includes plant or animal matter used for production of fibers, chemicals or heat. Biomass may also include biodegradable wastes that can be used as fuel. It is usually measured by dry weight. The term biomass is useful for plants, where some internal structures may not always be considered living tissue, such as the wood (secondary xylem) of a tree. This biomass became produced from plants that convert sunlight into plant material through photosynthesis. Sources of biomass energy lead to agricultural crop residues, energy plantations, and municipal and industrial wastes. The term "biomass," as used herein, excludes components of traditional media used to culture microorganisms, such as purified starch, peptone, yeast extract but includes waste material obtained during industrial processes developed to produce purified starch. According to the invention, biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn steep liquor, grasses, wheat, wheat straw, barley, barley straw, grain residue from barley degradation during brewing of beer, hay, rice straw, switchgrass, waste paper, sugar cane bagasse, sorghum, soy, components obtained from processing of grains, trees, branches, roots, leaves, wood chips, sawdust, shrubs and bushes, soybean hulls, vegetables, fruits, flowers and animal manure. In one embodiment, biomass that is useful for the invention includes biomass that has a relatively high carbohydrate value, is relatively dense, and/or is relatively easy to collect, transport, store and/or handle.

As used herein, the term "biomass by-products" refers to biomass materials that are produced from the processing of biomass.

As used herein, the term "bioreactor" refers to an enclosed or isolated system for containment of a microorganism and a biomass material. The "bioreactor" may preferably be configured for anaerobic growth of the microorganism.

As used herein, the term "hyperthermophilic organism" means an organism which grows optimally at temperatures above 80° C.

As used herein, the terms "degrade" and "degradation" refer to the process of reducing the complexity of a substrate, such as a biomass substrate, by a biochemical process, preferably facilitated by microorganisms (i.e., biological degradation). Degradation results in the formation of simpler compounds such as methane, ethanol, hydrogen, and other relatively simple organic compounds (i.e., degradation products) from complex compounds. The term "degradation" encompasses anaerobic and aerobic processes, including fermentation processes.

DETAILED DESCRIPTION OF THE INVENTION

The present invention relates to the field of biomass degradation with hyperthermophilic organisms, and in particular to the use of hyperthermophilic degradation to produce heat from a biomass. For convenience, the description of the invention is provided in the following section: A. Hyperthermophilic organism; B. Biomass; C. Degradation and energy production; and D. Carbon credit generation.

A. Hyperthermophilic Organisms

The present invention contemplates the use of hyperthermophilic organism for fermenting biomass. Thermophilic bacteria are organisms which are capable of growth at elevated temperatures. Unlike the mesophiles, which grow best at temperatures in the range of 25-40° C., or psychrophiles, which grow best at temperatures in the range of 15-20° C., thermophiles grow best at temperatures greater than 50° C. Indeed, some thermophiles grow best at 65-75° C., and some of the hyperthermophiles grow at temperatures up to 113° C. (See e.g., J. G. Black, *Microbiology Principles and Applications,* 2d edition, Prentice Hall, New Jersey, [1993] p. 145-146; Dworkin, M., Falkow, S., Rosenberg, E, Schleifer, K-H., Stackebarndt E. (eds) The prokaryotes, third edition, volume 3, p. 3-28296 and p. 797-814 and p. 899-

924; Madigan M., Martinko, J. Brock Biology of Microorganisms, eleventh edition, p. 430-441 and 414-415).

The thermophilic bacteria encompass a wide variety of genera and species. There are thermophilic representatives included within the phototrophic bacteria (i.e., the purple bacteria, green bacteria, and cyanobacteria), bacteria (i.e., *Bacillus, Clostridium, Thiobacillus, Desulfotomaculum, Thermus*, Lactic acid bacteria, *Actinomycetes, Spirochetes*, and numerous other genera), and many hyperthermophilic orders (i.e., *Pyrococcus, Thermococcus, Thermotoga, Sulfolobus*, and some methanogens). There are aerobic as well as anaerobic thermophilic organisms. Thus, the environments in which thermophiles may be isolated vary greatly, although all of these organisms are isolated from areas associated with high temperatures. Natural geothermal habitats have a worldwide distribution and are primarily associated with tectonically active zones where major movements of the earth's crust occur. Thermophilic bacteria have been isolated from all of the various geothermal habitats, including boiling springs with neutral pH ranges, sulfur-rich acidic springs, and deep-sea vents. In general, the organisms are optimally adapted to the temperatures at which they are living in these geothermal habitats (T. D. Brock, "Introduction: An overview of the thermophiles," in T. D. Brock (ed.), *Thermophiles. General, Molecular and Applied Microbiology*, John Wiley & Sons, New York [1986], pp. 1-16; Madigan M., Martinko, J. Brock Biology of Microorganisms, eleventh edition, p. 442-446 and p. 299-328). Basic, as well as applied research on thermophiles has provided some insight into the physiology of these organisms, as well as promise for use of these organisms in industry and biotechnology.

The present invention is not limited to the use any particular hyperthermophilic organism. In some embodiments, mixtures of hyperthermophilic organisms are utilized. In some embodiments, the hyperthermophiles are from the archaeal order *Thermococcales*, including but not limited to hyperthermophiles of the genera *Pyrococcus, Thermococcus*, and *Palaeococcus*. Examples of particular organisms within these genera include, but are not limited to, *Pyrococcus furiosus, Thermococcus barophilus, T. aggregans, T. aegaeicus, T. litoralis, T. alcaliphilus, T. sibiricus, T. atlanticus, T. siculi, T. pacificus, T. waiotapuensis, T zilligi, T. guaymasensis, T. fumicolans, T. gorgonarius, T. celer, T. barossii, T. hydrothermalis, T. acidaminovorans, T. prfundus, T. stetteri, T. kodakaraensis, T. peptonophilis*. In some embodiments, aerobic hyperthermophilic organisms such as *Aeropyrum pernix, Sulfolobus solfataricus, Metallosphaera sedula, Sulfobus tokodaii, Thermoplasma acidophilum* and *Thermoplasma volcanium* are utilized. While in other embodiments, anaerobic or facultative aerobic organisms such as *Pyrobaculum calidifontis* and *Pyrobaculum oguniense* are utilized. Other useful archaeal organisms include, but are not limited to, *Sulfolobus acidocaldarius* and *Acidianus ambivalens*. In some embodiments, the hyperthermophilic organisms are bacteria, such as *Thermus aquaticus, Thermus thermophilus, Thermus flavu, Thermus ruber, Bacillus caldotenax, Bacillus stearothermophilus, Anaerocellum thermophilus, Thermoactinomycees vulgaris*, and members of the order *Thermotogales*, including, but not limited to *Thermotoga elfeii, Thermotoga hypogea, Thermotoga maritima, Thermotoga neapolitana, Thermotoga subterranean, Thermotoga thermarum, Petrotoga miotherma, Petrotoga mobilis, Thermosipho africanus, Thermosipho melanesiensis, Fervidobacterium islandicum, Fervidobacterium nodosum, Fervidobacterium pennavorans, Fervidobacterium gondwanense, Geotoga petraea, Geotoga subterranea*.

In some embodiments, hyperthermophilic strains of the above organisms suitable for fermenting biomass will be selected by screening and selecting for suitable strains. In still further embodiments, suitable strains will be genetically modified to include desirable metabolic enzymes, including, but not limited to hydrolytic enzymes, proteases, alcohol dehydrogenase, and pyruvate decarboxylase. See, e.g., (Bra/u, B., and H. Sahm [1986] Arch. Microbiol. 146:105-110; Bra/u, B. and H. Sahm [1986] Arch. Microbiol. 144:296-301; Conway, T., Y. A. Osman, J. I. Konnan, E. M. Hoffmann, and L. O. Ingram [1987] J. Bacteriol. 169:949-954; Conway, T., G. W. Sewell, Y. A. Osman, and L. O. Ingram [1987] J. Bacteriol. 169:2591-2597; Neale, A. D., R. K. Scopes, R. E. H. Wettenhall, and N. J. Hoogenraad [1987] Nucleic Acid. Res. 15:1753-1761; Ingram, L. O., and T. Conway [1988] Appl. Environ. Microbiol. 54:397-404; Ingram, L. O., T. Conway, D. P. Clark, G. W. Sewell, and J. F. Preston [1987] Appl. Environ. Microbiol. 53:2420-2425). In some embodiments, a PET operon is introduced into the hyperthermophile. See U.S. Pat. No. 5,000,000, incorporated herein by reference in its entirety.

In some embodiments, hyperthermophiles that produce ethanol via degradation are selected. In some embodiments, such hyperthermophiles are selected in media containing progressively higher amounts of ethanol to select for strains with increased ethanol tolerance. Accordingly, some embodiments of the present invention provide hyperthermophiles with increased ethanol tolerance or increased ability to produce ethanol. In some preferred embodiments, the hyperthermophiles utilize lignocellulosic biomass. In further preferred embodiments, the hyperthermophile utilize glucose, xylose, arabinose, galactose, and mannose.

B. Biomass

The present invention contemplates the degradation of biomass with hyperthermophilic organisms. The present invention is not limited to the use of any particular biomass. Suitable biomass includes, but is not limited to, sewage, agricultural waste products, brewery grain by-products, food waste, organic industry waste, forestry waste, crops, grass, seaweed, plankton, algae, fish, fish waste, and combinations thereof. In some embodiments, the biomass is harvested particularly for use in hyperthermophilic degradation processes, while in other embodiments waste or by-products materials from a pre-existing industry are utilized.

In some preferred embodiments, the biomass is lignocellulosic. In some embodiments, the biomass is pretreated with cellulases or other enzymes to digest the cellulose. In some embodiments, the biomass is pretreated by heating in the presence of a mineral acid or base catalyst to completely or partially hydrolyze hemicellulose, decrystallize cellulose, and remove lignin. This allows cellulose enzymes to access the cellulose.

In still other preferred embodiments, the biomass is supplemented with minerals, energy sources or other organic substances. Examples of minerals include, but are not limited, to those found in seawater such as NaCl, $MgSO_4 \times 7H_2O$, $MgCl_2 \times 6H_2O$, $CaCl_2 \times 2H_2O$, KCl, NaBr, $H_3BO_3$ and $SrCl_2 \times 6H_2$) and other minerals such as $MnSO4 \times H_2O$, $FeSO_4 \times 7H_2O$, $CoSO_4 \times 7H_2O$, $ZnSO_4 \times 7H_2O$, $CuSO_4 \times 5H_2O$, $KAl(SO_4)2 \times 12H_2O$, $Na_2MoOSO_4 \times 2H_2O$, $(NHSO_4)_2Ni(SO_4)_2 \times 6H_2O$, $Na_2WO_4 \times 2H_2O$ and $Na_2SeO_4$. Examples of energy sources and other substrates include, but are not limited to, purified sucrose, fructose, glucose, starch, peptone, yeast extract, amino acids, nucleotides, nucleosides, and other components commonly included in cell culture media.

C. Degradation and Energy Production

In preferred embodiments of the present invention, one or more populations of hyperthermophilic organisms are utilized to degrade biomass. In some embodiments, the biomass is transferred to a vessel such as a bioreactor and inoculated with one or more strains of hyperthermophilic organisms. In some embodiments, the environment of the vessel is maintained at a temperature, pressure, and pH sufficient to allow the strain(s) to metabolize the feedstock. In some preferred embodiments, the environment has no added sulfur or inorganic sulfide salts or is treated to remove or neutralize such compounds. In some preferred embodiments, the environment is maintained at a temperature above 45° C. In still further embodiments, the environment the environment is maintained at between 55° C. and 90° C. In some preferred embodiments, sugars, starches, xylans, celluloses, oils, petroleums, bitumens, amino acids, long-chain fatty acids, proteins, or combinations thereof, are added to the biomass. In some embodiments, water is added to the biomass to form an at least a partially aqueous medium. In some embodiments, the aqueous medium has a dissolved oxygen gas concentration of between about 0.2 mg/liter and 2.8 mg/liter. In some embodiments, the environment is maintained at a pH of between approximately 4 and 10. In some embodiments, the environment is preconditioned with an inert gas selected from a group consisting of nitrogen, carbon dioxide, helium, neon, argon, krypton, xenon, and combinations thereof. While in other embodiments, oxygen is added to the environment to support aerobic degradation.

In some embodiments, where lignocellulosic material are utilized, the cellulose is pre-treated as described above. The pre-treated cellulose is enzymatically hydrolyzed either prior to degradation in sequential saccharification and degradation or by adding the cellulose and hyperthermophile inoculum together for simultaneous saccharification and degradation.

It is contemplated that degradation of the biomass will both directly produce energy in the form of heat as well as produce products that can be used in subsequent processes, including the production of energy. In some embodiments, hydrogen, methane, and ethanol are produced by the degradation and utilized for energy production. In preferred embodiments, these products are removed from the vessel. It is contemplated that removal of these materials in the gas phase will be facilitated by the high temperature in the culture vessel. These products may be converted into energy by standard processes including combustion and/or formation of steam to drive steam turbines or generators. In some embodiments, the hydrogen is utilized in fuel cells. In some embodiments, proteins, acids and glycerol are formed which can be purified for other uses or, for, example, used as animal feeds.

In some embodiments, the degradation products are removed from the vessel. It is contemplated that the high temperatures at which the degradation can be conducted facilitate removal of valuable degradation products from the vessel in the gas phase. In some embodiments, methane, hydrogen and/or ethanol are removed from the vessel. In some embodiments, these materials are moved from the vessel via a system of pipes so that the product can be used to generate power or electricity. For example, in some embodiments, methane or ethanol are used in a combustion unit to generate power or electricity. In some embodiments, steam power is generated via a steam turbine or generator.

In some embodiments, the products are packages for use. For example, the ethanol, methane or hydrogen can be packaged in tanks or tankers and transported to a site remote from the fermenting vessel. In other embodiments, the products are fed into a pipeline system.

In still other embodiments, heat generated in the vessel is utilized. In some embodiments, the heat generated is utilized in radiant system where a liquid is heated and then circulated via pipes or tubes in an area requiring heating. In some embodiments, the heat is utilized in a heat pump system. In still other embodiments, the heat is utilized to produce electricity via a thermocouple. In some embodiments, the electricity produced is used to generate hydrogen via an electrolysis reaction.

D. Carbon Credit Trading

In some embodiments, the present invention provides methods for generating carbon credits for trading in established carbon credit trading programs such as those established under the Kyoto protocol. The European Union Emission Trading System (EU ETS), which began operation in January 2005, is the largest multi-national, multi-sector greenhouse gas emissions trading scheme in the world. The system was set up as the EU's response to the Kyoto Protocol to the United Nations Framework Convention on Climate Change which was negotiated in 1997 and ratified in 2005. It is a commitment among participating industrialised nations to curb the rise in global temperature by abating their emissions of six greenhouse gases including carbon dioxide, methane, nitrous oxide, sulfur hexafluoride, perfluorocarbons (PFCs) and hydrofluorocarbons (HFCs). To date, 162 nations have ratified the agreement. Notable exceptions are the United States and Australia. Furthermore, two of the fastest growing economies, India and China, are not required to reduce their carbon emissions under the current agreement.

The Kyoto Protocol provides three implementation mechanisms to regulate greenhouse gas emissions. The first, International Emissions Trading (IET), permits countries below their current emissions limits to sell their excess allowances to other countries on the open market. The second, Joint Implementation (JI), allows investors from industrialised countries financing greenhouse gas emissions reduction projects in other industrialised countries to receive emission credits called "emissions reduction units" (ERUs). The third, Clean Development Mechanism (CDM), lets investors from industrialised countries accumulate "certified emission reduction units" (CERs) for helping finance carbon reduction projects in developing countries.

The EU ETS exists in two phases and encompasses all of the high use energy and power sectors. The first phase, which started in 2005 and will end in 2007, allows for the trade of $CO_2$ allowances with the potential to expand into the other five greenhouse gasses. So far, it has set caps on the emissions of 12,000 to 15,000 industrial installations across Europe. It covers 45% of emission activities including power, concrete, pulp, paper, and ferrous metals. The second phase, from 2008 to 2012, could possibly cover all greenhouse gases and installations, and will include JI and CDM credits in the market. It is important to note that in the first phase an amendment called the Linking Directive was implemented which enabled installations to use CERs and ERUs from JI and CDM to meet their emission targets.

The EU ETS is monitored and regulated by the EU Commission (EUC). In both phases, the EUC places limitations on GHG which are satisfied through the trading of EU emission allowances (EUAs). The goal is to force companies to find the lowest cost of abatement by decreasing their GHG internally and selling any unused EUAs into the market. During the first phase, the EUC imposes a penalty of € 40 per ton of CO2 for installations that emit more than their target limit. In addition, these installations must acquire their excess emissions in the market. This penalty will go to € 100 per ton of CO2 in the second phase.

Participating countries in the EU ETS submit their target GHG reductions through National Allocation Plans (NAPs) which then are approved by the EUC. According to the Norwegian consultant Point Carbon, during the first phase of the EU ETS, the EUC approved circa 6.3 billion allowances and allowed for another 2.1 billion to be distributed each year.

As one example of an established system, the European Bank for Reconstruction and Development (EBRD) and the European Investment Bank (EIB) established the Multilateral Carbon Credit Fund (MCCF) for countries from Central Europe to Central Asia.

By joining the MCCF, private and public companies as well as EBRD and EIB shareholder countries can purchase carbon credits from emission reduction projects financed by the EIB or EBRD to meet their mandatory or voluntary greenhouse gas (GHG) emission reduction targets.

In addition to the project credits, countries can also participate via the MCCF in green investment schemes. This is an innovative way to facilitate government-to-government trade in carbon credits, whereby the selling country uses the revenue from the sale of carbon credits to support investments in climate-friendly projects. Carbon credits can be generated from a large variety of project types, all of which reduce or avoid GHG emissions. These include credits produced from renewable energy such as wind, hydro, biogas (from landfills/wastewater) and biomass.

In some embodiments, the present invention generates carbon credits for trading by utilizing biomass. In other embodiments, the present invention generates carbon credits for trading by utilizing materials that would otherwise create methane that is subsequently released into the atmosphere, such as manure, sewage, waste water, landfilled materials and the like. The present invention is not limited to any particular mechanism of action. Indeed, an understanding of the mechanism of action is not needed to practice the present invention. Nevertheless, it is contemplates that the use of hyperthermophilic organisms in an anaerobic degradation process is highly efficient for reducing carbon emissions, and in particular emissions of carbon dioxide. In particular, the use of anaerobic degradation reduces the amount carbon dioxide released from biomass by about six-fold as compared to aerobic degradation or fermentation processes.

In some embodiments, the present invention provides a system wherein energy is produced by degradation of biomass with hyperthermophilic organisms, and resulting carbon credits generated through the use of the system are used to offset greenhouse gas emissions by conventional energy production systems such as combustion of coal, natural gas, and oil. In some embodiments, the energy production systems are under the control of a single entity, while in other embodiments, the energy production systems are under the control of separate entities and the carbon credits are purchased by or traded to the entity generating power by conventional means with fossil fuels.

EXPERIMENTAL

1. Selection of Hyperthermophilic Organisms for Degradation Processes

In this example, strains of hyperthermophilic organisms from the genera *Pyrococcus, Thermococcus, Palaeococcus, Aeropyrum pernix, Sulfolobus, Pyrobaculum, Pyrolobus, Pyrodictium, Thermus, Bacillus stearothermophilus, Metallosphaera, Anaerocellum, Thermoactinomyces, Thermotoga, Fervidobacterium* and *Geotoga* are selected and screened for the ability to produce fermentation byproducts ethanol, methanol and hydrogen. Briefly, seed inoculums are prepared by culturing the cells in YT medium (yeast extract [2.0 g/liter], tryptone [4.0 g/liter], $Na_2S_2O_3$ [0.61 g/liter], and ASN-III salts) for 48 h. Flasks containing base medium (tryptone (4.0 g/liter), $Na_2S_2O_3$ (0.61 g/liter), and ASN-III salts (artificial seawater salts containing NaCl [29.8 g/liter], $MgCl_2$ [1.1 g/liter], $MgSO_4$ [2.0 g/liter], $CaCl_2$ [0.45 g/liter], KCl [0.6 g/liter], and $Na_2CO_3$ [0.024 g/liter])(pH 7.0)) supplemented with specific carbohydrates (glucose, xylose, arabinose, galactose, and/or mannose) (3.0 g/liter) are inoculated with 10% seed inoculums. The flasks are then purged with prepurified $N_2$ and the incubation is carried out at 90° C.-110° C. in a rotary shaker at 150 rpm. Cell growth is observed by monitoring optical density at 660 nm ($OD_{660}$). Samples are collected from the headspace and culture medium and analyzed by GC for fermentation products.

2. Growth of *Pyrococcus furiosus* and *Thermotoga maritima* on Waste Materials and Biomass Substrates The hyperthermophilic archaeon *Pyrococcus furiosus* (growth range 67-103° C., optimal growth at 100° C.) uses simple and complex carbohydrates and converts them to acetate, to $C0_2$ and to $H_2$. Only in the presence of elemental sulphur (S°), $H_2$ is used to reduce sulphur to $H_2S$. An exponentially growing culture produces ~1 µmol $ml^{-1}h^{-1}$ $H_2$ (Schut et al., 2007, J. Bacteriol 189, 4431-4441). Growth experiments in the laboratory have shown that the strain requires peptone and yeast extract (as protein and vitamin source) in addition for good growth ($2.2 \times 10^8$ cells/ml). On starch as sole carbon source only poor growth was observed (~$5 \times 10^7$ cells/ml).

*Thermotoga maritima* is an obligately anaerobic hyperthermophilic bacterium growing between 55-90° C. (growth optimum at 80° C.). Like *Pyrococcus* it is of marine origin and is cultivated in media resembling seawater. *Thermotoga* is an obligate heterotroph preferentially fermenting carbohydrates or complex organic matter. Fermentation of glucose by cell suspensions of *Thermotoga* yielded 118 mol L-(+) lactate, 47 mol acetate, 54 mol $C0_2$ and 9 mol $H_2$ (Huber et al., 1986, Arch. Microbiol. 144, 324-333). Some of the members of the *Thermotogales* like *Fervidobacterium nodosum* (Patel et al., 1985 Arch. Microbiol. 141, 63-69) and *Fervidobacterium islandicum* (Huber et al., Arch. Microbiol. 1990, 154, 105-111) have been described to produce also ethanol. *F. nodosum* forms after 13 h growth on glucose ~25 µmol ethanol per 10 ml culture broth (Patel et al., 1985). A quantitative analysis of fermentation products (micromole of product formed per 10 ml culture) of *T. nodosum* grown on glucose revealed: Ethanol 10, acetate 115, lactate 162, $CO_2$ 120 and $H_2$ 160 per 133 micromol glucose consumed.

Both organisms do not completely oxidize organic matter to $CO_2$. The carbon of the substrate is in part converted to soluble compounds like acetate and lactate. Both organism produce low amounts of hydrogen and soluble compounds like acetate. Some members of the *Thermotogales* have been described to produce ethanol in addition (*Fervidobacterium*). Thus these anaerobic organisms have the potential to synthesize energy rich compounds like $H_2$ and ethanol. The amount of $CO_2$ produced during anaerobic degradation of biomass is significantly lower than $CO_2$ release during aerobic processes which lead to complete oxidation of organic matter to $CO_2$. Methane formation will not occur during this process when pure cultures are used or when the waste substrate is sterilized. Otherwise methane might be formed from the end products formed by degradation of organic matter from *Thermotoga* and *Pyrococcus* ($H_2/CO_2$ and acetate). Acetate can be also converted to methane but no hyperthermophilic methanogen growing on acetate has been described. Therefore, it is unlikely that methane is formed from acetate when the fermentation will be conducted at temperatures between 80 and 100° C.

The objective was to investigate the potential of *P. furiosus* and *T. maritima* as model systems for the degradation of waste products and to investigate their ability to produce and to release heat during growth. The degradation of various waste products was studied in 100 l batch cultures. The energy release during growth was measured in a 10 l glass fermentor. The heating system of this fermentor was modified to lower the input of energy. The fermentor was isolated by the use of an aluminium containing shell and further isolated by styrene. As a control, heat release by a 10 l culture of *Saccharomyces cerevisiae* was also measured using this system.

| Utilization of waste substrates | | |
|---|---|---|
| | Pyrococcus | Thermotoga |
| Grain residues (from a brewery) | no growth | poor growth ($8 \times 10^6$ ml$^{-1}$) |
| Mixture of grain residues and whey | no growth | good growth $1.4 \times 10^8$ no pH control $3.2 \times 10^8$ w/ pH control |
| Mixture of grain residues and fish innards | $1 \times 10^8$ | $2 \times 10^8$ |
| Mixture of soluble starch and whey | ~$1 \times 10^8$ (final cell density was not determined) | not analyzed |

Detailed formulations of the culture media are provided below.

Since ethanol production has been described for some members of the *Thermotogales* we assayed also ethanol formation during growth on several substrates. We could not detect significant ethanol formation. For ethanol production, *Fervidobacterium* strains (*F. nodosum* and *F. islandicum*) may be utilized.

Heat Production During Growth

The measurement of energy release using a standard fermentor was difficult. When *Pyrococcus* was growing in the fermentor an input of 1060 Wh was required during an incubation time of 30 h to keep the temperature of the 10 l fermentor constantly at 90° C. In the absence of growing *Pyrococcus* cells the energy input in 30 h was 1140 Wh. This indicates an energy input of 35.5 W per hour in the absence of growing cells and 32.5 W per hour in the presence of growing cells. When the heat production was measured during growth of *Thermotoga* no energy release by growing cells could be detected, although the microorganisms grew quite well up within 13.5 hours to a cell density of $4 \times 10^8$ cells/ml.

It is known that large fermentors used for biotechnological processes like ethanol fermentation by yeast require cooling due to the energy released by growing yeast. To control the system for the detection of heat production we grew yeast anaerobically at 30° C. During 95 h after inoculation of the medium no external energy input was required to keep the growth temperature at 30° C. and the temperature of the culture medium was even increased by 0.5° C. This finding suggests that the detecting system is suitable to measure energy release by microorganisms. To confirm the validity of our measurement it is advisable to repeat the experiment in an air conditioned room (room temperature fixed at 20° C.).

3. *Pyrococcus Furiosus* ½ SME Medium

| ½ SME | |
|---|---|
| Component | Amount |
| SME | 500.0 ml |
| $KH_2PO_4$ | 0.5 g |
| Wolfe's mineral elixir/ 10x/pH 6.5/new + T | 1.0 ml |
| Resazurin, 0.1% solution | 1.0 ml |
| $Na_2S \times 7\text{-}9H_2O$ | 0.5 g |
| $H_2O$ 2 × distilled, add to a final volume of | 1000.0 ml |

| Synthetic Seawater - SME | | |
|---|---|---|
| Component | Amount | concentration |
| NaCl | 27.7 g | 473.99 mM |
| $MgSO_4 \times 7H_2O$ | 7.0 g | 28.4 mM |
| $MgCl_2 \times 6H_2O$ | 5.5 g | 27.1 mM |
| $CaCl_2 \times 2H_2O$ | 0.75 g | 5.1 mM |
| KCl | 0.65 g | 8.7 mM |
| NaBr | 0.1 g | 0.97 mM |
| $H_3BO_3$ | 0.03 g | 0.49 mM |
| $SrCl_2 \times 6H_2O$ | 0.015 g | 0.056 mM |
| KJ-Lsg., 0.05% ig | 0.1 ml | 0.30 μM |
| $H_2O$ 2 × distilled, add to a fnal volume of | 1000.0 ml | |

| Wolfe's mineral elixir 10x/pH 6.5/new + Titriplex | | |
|---|---|---|
| Component | amount | concentration |
| Titriplex 1 (Nitrilotriacetic acid) | 15.0 g | 78.50 mM |
| $MgSO_4 \times 7H_2O$ | 30.0 g | 121.70 mM |
| $MnSO_4 \times H_2O$ | 5.0 g | 29.60 mM |
| NaCl | 10.0 g | 171.10 mM |
| $FeSO_4 \times 7H_2O$ | 1.0 g | 3.60 mM |
| $CoSO_4 \times 7H_2O$ | 1.8 g | 6.40 mM |
| $CaCl_2 \times 2H_2O$ | 1.0 g | 6.80 mM |
| $ZnSO_4 \times 7H_2O$ | 1.8 g | 6.30 mM |
| $CuSO_4 \times 5H_2O$ | 0.1 g | 0.40 mM |
| $KAl(SO_4)_2 \times 12H_2O$ | 0.18 g | 0.38 mM |
| $H_3BO_3$ | 0.1 g | 1.62 mM |
| $Na_2MoO_4 \times 2H_2O$ | 0.1 g | 0.41 mM |
| $(NH_4)_2Ni(SO_4)_2 \times 6H_2O$ | 2.80 g | 7.09 mM |
| $Na_2WO_4 \times 2H_2O$ | 0.1 g | 0.30 mM |
| $Na_2SeO_4$ | 0.1 g | 0.53 mM |
| $H_2O$ add to a final volume of | 1000.0 ml | |

In standard medium, the following organic substrates were added:

| Component | Amount |
|---|---|
| Yeast extract (Difco) | 0.1% |
| Pepton from casein (Difco) | 0.1% |
| Starch (Merck) | 0.1% |

For *Pyrococcus furiosus*: pH: 7.0
Headspace: $N_2/CO_2$

To study utilization of waste products we replaced the organic components of the medium by various waste materials: grain residues: 5%; whey 10%; fish innards 0.95%

4. *Thermotoga* MM-I-Medium

| MM-I-medium | |
|---|---|
| Compound | Amount |
| SME | 250.0 ml |
| $KH_2PO_4$ | 0.5 g |
| $(NH_4)_2SO_4$ | 0.5 g |
| $NaHCO_3$ | 0.1 g |
| Wolfe's mineral elixir, 10×/pH 6.5/new + T | 1.5 ml |
| Resazurin, 0.1% solution | 1.0 ml |
| $Na_2S \times 7\text{-}9H_2O$ | 0.5 g |
| $H_2O$ 2 × distilled, add to a final volume of | 1000.0 ml |

| Synthetic Seawater - SME | | |
|---|---|---|
| Compound | Amount | Concentration |
| NaCl | 27.7 g | 473.99 mM |
| $MgSO_4 \times 7H_2O$ | 7.0 g | 28.4 mM |
| $MgCl_2 \times 6H_2O$ | 5.5 g | 27.1 mM |
| $CaCl_2 \times 2H_2O$ | 0.75 g | 5.1 mM |
| KCl | 0.65 g | 8.7 mM |
| NaBr | 0.1 g | 0.97 mM |
| $H_3BO_3$ | 0.03 g | 0.49 mM |
| $SrCl_2 \times 6H_2O$ | 0.015 g | 0.056 mM |
| KJ-solution., 0.05% (w/v) | 0.1 ml | 0.30 μM |
| $H_2O$ 2 × distilled, add to a final volume of | 1000.0 ml | |

| Wolfe's mineral elixir 10×/pH 6.5/new + Titriplex | | |
|---|---|---|
| Compound | amount | concentration |
| Titriplex 1 (Nitrilotriacetic acid) | 15.0 g | 78.50 mM |
| $MgSO_4 \times 7H_2O$ | 30.0 g | 121.70 mM |
| $MnSO_4 \times H_2O$ | 5.0 g | 29.60 mM |
| NaCl | 10.0 g | 171.10 mM |
| $FeSO_4 \times 7H_2O$ | 1.0 g | 3.0 mM |
| $CoSO_4 \times 7H_2O$ | 1.8 g | 6.40 mM |
| $CaCl_2 \times 2H_2O$ | 1.0 g | 6.80 mM |
| $ZnSO_4 \times 7H_2O$ | 1.8 g | 6.30 mM |
| $CuSO_4 \times 5H_2O$ | 0.1 g | 0.40 mM |
| $KAl(SO_4)_2 \times 12H_2O$ | 0.18 g | 0.38 mM |
| $H_3BO_3$ | 0.1 g | 1.62 mM |
| $Na_2MoO_4 \times 2H_2O$ | 0.1 g | 0.41 mM |
| $(NH_4)_2Ni(SO_4)_2 \times 6H_2O$ | 2.80 g | 7.09 mM |
| $Na_2WO_4 \times 2H_2O$ | 0.1 g | 0.30 mM |
| $Na_2SeO_4$ | 0.1 g | 0.53 mM |
| $H_2O$ 2 × distilled, add to a final volume of | 1000.0 ml | |

For growth of *Thermotoga maritima* the following organic substrates were added:

| Compound | amount |
|---|---|
| Starch (Merck 101252.1000) | 0.05% |
| Yeast extract (Difco) | 0.05% |

To study growth on waste products the organic substrates were replaced by: grain residues (5% w/w), whey 10% (v/v) and homogenized fish innards 0.9% (950 g/100 l).

pH: 7.0 headspace: $N_2$

In some experiments first growth of *Pyrococcus* was studied at 90° C., if *Pyrococcus* failed to grow or after growth of *Pyrococcus* to $1 \times 10^8$ cells/ml the medium was cooled down to 80° C. and then the same medium was inoculated with *Thermotoga*. On the substrate mixture grain residues and fish innards good growth of *Thermotoga* was observed under these conditions; this indicates that *Thermotoga* grows well in *Pyrococcus* medium.

The invention claimed is:

1. A method comprising:
   a) providing an algal biomass and a population of hyperthermophilic *Thermatoga* spp.;
   b) degrading said biomass in the presence of said population of hyperthermophilic *Thermatoga* spp. at a temperature of above 80° C. under conditions such that degradation products are produced.

2. The method of claim 1, wherein said degradation products are selected from the group consisting of hydrogen, methane and acetate.

3. The method of claim 2, further comprising using said hydrogen in a fuel cell.

4. The method of claim 2, further comprising using said methane in a combustion unit.

5. The method of claim 1, further comprising the step of converting said degradation products into energy.

6. A method for reducing carbon dioxide emissions comprising:
   a) providing an algal biomass and a population of hyperthermophilic *Thermatoga* spp.;
   b) anaerobically degrading said biomass in the presence of said population of hyperthermophilic *Thermatoga* spp. at a temperature of above 80° C. to produce substrates for energy production;
   c) producing energy from said substrates, wherein carbon dioxide emissions are reduced as compared to aerobic degradation of said biomass materials.

7. A method for generating carbon credits comprising:
   a) providing an algal biomass and a population of hyperthermophilic *Thermatoga* spp.;
   b) anaerobically degrading said biomass in the presence of said population of hyperthermophilic *Thermatoga* spp. at a temperature of above 80° C. to produce substrates for energy production,
   c) producing energy from said substrates under conditions such that carbon credits are generated.

\* \* \* \* \*